US010005006B2

(12) United States Patent
Hochgraeber et al.

(10) Patent No.: US 10,005,006 B2
(45) Date of Patent: Jun. 26, 2018

(54) METHOD FOR ADJUSTING A GRADIENT DELAY VOLUME

(71) Applicant: DIONEX SOFTRON GMBH, Germering (DE)

(72) Inventors: Hermann Hochgraeber, Offenberg (DE); Thomas Wachinger, Altomuenster (DE)

(73) Assignee: DIONEX SOFTRON GMBH, Germering (DE)

( * ) Notice: Subject to any disclaimer, the term of this patent is extended or adjusted under 35 U.S.C. 154(b) by 408 days.

(21) Appl. No.: 14/661,793

(22) Filed: Mar. 18, 2015

(65) Prior Publication Data

US 2015/0265944 A1    Sep. 24, 2015

(30) Foreign Application Priority Data

Mar. 19, 2014   (DE) .................. 10 2014 103 766

(51) Int. Cl.
*G01N 30/34* (2006.01)
*B01D 15/16* (2006.01)
*B01D 15/14* (2006.01)

(52) U.S. Cl.
CPC .......... *B01D 15/166* (2013.01); *G01N 30/34* (2013.01)

(58) Field of Classification Search
CPC ........ G01N 30/86; G01N 30/58; G01N 30/65; G01N 30/75; G01N 30/88; G01N 30/93;
(Continued)

(56) References Cited

U.S. PATENT DOCUMENTS 5,040,126 A * 8/1991 Allington ............... G01N 30/32
                                                                 210/659
5,089,124 A * 2/1992 Mahar .................... G01N 30/34
                                                                 210/101
(Continued)

FOREIGN PATENT DOCUMENTS

DE           10393856        2/2006
DE         102008006266      8/2009
(Continued)

OTHER PUBLICATIONS

Hendriks et al., "New practical algorithm for modelling retention times in gradient reversed-phase high-performance liquid chromatography," J of Chromatography A, 1089, 193-202, 2005.
(Continued)

*Primary Examiner* — Pamela H Weiss

(57) ABSTRACT

The invention relates to a method for setting a gradient delay volume GDV of a liquid chromatography system for a chromatography run in liquid chromatography, in particular a high-performance liquid chromatography system, in which a desired value $GDV_{target}$ of a gradient delay volume of the liquid chromatography system is ascertained or predefined and, if the value $GDV_{target}$ deviates from a specific fixed value $GDV_{actual}$ of a liquid chromatography system, this value $GDV_{target}$ is set in a range $0 \leq \Delta GDV = GDV_{target} - GDV_{actual} \leq V_{max}$ of a volume of a volume adjustment device 5. Furthermore, the invention relates to an automatic sampler for carrying out such a method.

8 Claims, 7 Drawing Sheets

(58) Field of Classification Search
CPC ........ G01N 30/96; G01N 86/58; G01N 86/65; G01N 86/75; G01N 86/88; G01N 86/93; G01N 86/96; G01N 30/34; B01D 15/166
See application file for complete search history.

(56) References Cited

U.S. PATENT DOCUMENTS

| | | | |
|---|---|---|---|
| 6,712,085 | B2 | 3/2004 | Weissgerber et al. |
| 6,780,315 | B2 | 8/2004 | Richardson et al. |
| 8,515,587 | B2 | 8/2013 | Witt et al. |
| 8,806,922 | B2 | 8/2014 | Hochgraeber |
| 9,086,426 | B2 | 7/2015 | Liu et al. |
| 9,188,573 | B2 | 11/2015 | Liu et al. |
| 9,435,773 | B2 | 9/2016 | Glatz et al. |
| 2002/0010566 | A1* | 1/2002 | Chester .............. G01N 30/8693 703/2 |
| 2003/0116195 | A1 | 6/2003 | Weissgerber et al. |
| 2003/0143123 | A1* | 7/2003 | Maeda .................. G01N 30/24 422/510 |
| 2003/0165941 | A1* | 9/2003 | Gjerde ................ B01D 15/366 435/6.12 |
| 2007/0183928 | A1* | 8/2007 | Neyer .................... G01N 30/32 422/70 |
| 2010/0252502 | A1* | 10/2010 | Witt .................... F04B 11/0058 210/656 |
| 2011/0005304 | A1* | 1/2011 | Vorm ................... B01D 15/163 73/61.52 |
| 2011/0209766 | A1* | 9/2011 | Witt ........................ G01N 30/34 137/1 |
| 2012/0096919 | A1* | 4/2012 | Choikhet ............... G01N 30/24 73/1.02 |
| 2013/0078625 | A1* | 3/2013 | Holmes .............. G01N 35/0092 435/6.11 |
| 2014/0060162 | A1 | 3/2014 | Clarke et al. |

FOREIGN PATENT DOCUMENTS

| | | | |
|---|---|---|---|
| DE | 102009029028 | 5/2010 | |
| EP | 0132403 B1 | 3/1993 | |
| EP | 01324033 B1 | 7/2003 | |
| WO | WO 2010139359 A1 * | 12/2010 | ............. G01N 30/20 |
| WO | WO2012099763 A1 | 7/2012 | |

OTHER PUBLICATIONS

Guillarme, "Method transfer for fast liquid chromatography in pharmaceutical analysis: Application to short columns packed with small particle. Part II: Gradient experiments," European Journal of Pharmaceutics and Biopharmaceutics, vol. 68, pp. 430-440, 2008.

* cited by examiner

METHOD FOR ADJUSTING A GRADIENT DELAY VOLUME

CROSS REFERENCE TO RELATED APPLICATIONS

This application claims the priority benefit under 35 U.S.C. § 119 to German Patent Application No. 10 2014 103 766.9, by Hermann Hochgraeber and Thomas Wachinger for "A method of adjusting a gradient delay volume" filed on Mar. 19, 2014, the disclosure of which is incorporated herein by reference.

FIELD OF THE INVENTION

The present invention is in the field of liquid chromatography, in particular high-performance liquid chromatography (HPLC).

BACKGROUND

Liquid chromatography (in particular HPLC) is used for the purpose of separating liquid samples into their components by means of a chromatography column. In this case, the separating power of the (separating) column is dependent, inter alia, on its length and on the particle size of the packing material. For the best possible separation, columns having a sufficient length and a small particle size are required. Such columns have a high flow resistance and therefore require substantially higher pressures for operation than conventional columns.

Furthermore, a sufficiently rapid separation is desirable, to enable a high sample throughput. This requires a high flow speed in the column, whereby the counterpressure in the column also increases.

One possibility for accelerating the separation or increasing the separating power is to change the solvent composition over the duration of the separation (referred to hereafter as the gradient, i.e., the degree of the change of the elution force or the proportion of a solvent with time is referred to as the gradient or solvent gradient).

Two different technical implementations for achieving a gradient have prevailed due to the different requirements for the separation. These are so-called high-pressure gradient forming (HPG) and low-pressure gradient forming (LPG). High-pressure gradient forming operates by means of two independent pumps, which are connected to one another via a T-part on the high-pressure side of the system. The gradient is generated by way of the change of the flow rates at the two pumps. Low-pressure gradient forming only requires one pump having proportioning valve unit connected upstream. During the aspirating cycle of the pump, the various solvents are drawn successively into the pump by opening and closing the valves (for example, solenoid valves) in the proportioning valve unit. The gradient is formed due to the variations in the opening times for the various solvents. To smooth out composition fluctuations in the solvent mixture (mixture irregularity), a mixer is connected downstream from the pump as a standard feature.

In the various designs, there are different so-called gradient delay volumes (GDV—or also dwell volume). The gradient delay volume or mixing volume is dimensioned, on the one hand, by way of the holding capacity of all interconnected components from the mixing point up to the entry of the column. In the case of LPG, the GDV—depending on the implementation of the switching valve and the connecting ports which are switched through—is formed, for example, by the volumes of the following components (or a part thereof): pump head, mixer, connecting capillaries, sample loop, switching valve, metering device. In the case of HPG, the GDV—depending on the implementation of the switching valve and the connecting ports which are switched through—is formed, for example, by the volumes of the following components (or a part thereof): T-part, mixer, connecting capillaries, sample loop, switching valve, metering device. On the other hand, the washing-out volume must also be considered, which results due to the flow properties of the components.

If a chromatographic method was developed on a specific HPLC system, it usually cannot be transferred to another system without problems. The reproduction of a published method is also just as difficult. One cause of this is the different GDVs, which are accompanied by a shift and/or spreading of the retention times.

Furthermore, the mixture irregularity is also dependent on the GDV. The higher the GDV, the better the various solvents are mixed and the less the mixture irregularity.

The requirements for the GDV and the remaining mixture irregularity are also strongly dependent on the application and the detector type used. Non-optical detectors, such as MS, ELSD, or CAD, are typically insensitive to mixture irregularities, since these do not generate signal variations due to differing detection sensitivities to the individual solvent components. A mixer having small GDV with moderate mixer performance would therefore be acceptable in such a case. The situation appears very different, however, upon the use of a UV detector, above all at low wavelengths. Extremely small variations of the solvent composition have effects here in visible variations in the baseline. This makes it more difficult to determine the material concentration from the detector signal. A mixer having the highest possible mixing efficiency with correspondingly greater GDV would be advantageous in this case.

An unnecessarily large GDV is also advantageous, since the analysis, washing, and equilibration phases would also be increased unnecessarily.

If a method is transferred to another HPLC system, which has deviating GDVs, an offset time (tgdv=Vgdv/flow rate) could be calculated and the gradient forming could be started delayed or early accordingly.

However, problems with the irregularity cannot be completely remedied in this way. For this purpose, the mixer is normally manually replaced with another mixer. Of course, automation of such a replacement by means of a switching valve would also be conceivable. This solution would be cumbersome because of the size of the mixers and additionally costly, however.

SUMMARY

The present invention is therefore based on the object of providing a method and a system or an automatic sampler for carrying out this method, which enable an adaptation of the GDV or mixing volume in a cost-effective and structurally simple manner.

According to the invention, in a chromatography system between mixing point (gradient occurrence) and entry of a separating column, a volume adjustment device is provided, which enables simple, automated, and cost-effective change of the GDV or mixing volume. Such a volume adjustment device offers a preferably continuously settable volume, for example, via a control device, through which a solvent (gradient), which changes in composition, flows through during a chromatography run and correspondingly counts for the GDV.

Depending on the implementation of the chromatography system, components are located in the path—in or through which a gradient is navigated—for example:

in LPG—depending on the implementation of the switching valve and the connecting ports which are switched through: pump head, mixer, connecting capillaries, sample loop, switching valve, metering device, or parts thereof and;

in HPG—depending on the implementation of the switching valve and the connecting ports which are switched through: T-part, mixer, connecting capillaries, sample loop, switching valve, metering device, or parts thereof.

The holding capacity or the internal volume through which a gradient flows of the components located in each case in this path therefore result in a specific GDV for a respective system.

By way of the method according to the invention and by way of the liquid chromatography system according to the invention it is now possible to provide a desired GDV—deviating from a system-specific (fixed) GDV. Thus, a predefined GDV, which is ascertained during a method development or is known, for example, of another system can be set, without components (mixers, etc.) having to be changed, added, replaced, or switched for this purpose on the present system. The change of the GDV is performed in this case in a range between the maximum and minimum adjustable volumes, for example, 0 µL to 1000 µL, in particular 0 µL to 500 µL, preferably 0 µL to 120 µL, of the volume adjustment device, preferably by means of an electronic control unit.

In a further embodiment of the invention, the desired value is continuously adjustable by corresponding adjustment of the volume adjustment device. Of course, it is also conceivable to provide discrete steps within the variable range of the GDV, however.

In a preferred embodiment of the invention, a metering device which is already provided in the system, in particular in the automatic sampler, for taking samples and/or injecting samples, is used as the volume adjustment device. The additional use of an already provided component enables a structural and cost-reducing savings potential.

In an arbitrary embodiment of the invention, the desired GDV can be preset before a chromatography run (in which a gradient is navigated), for example, before taking a sample or before injecting a sample, or can be set during an injection or during a chromatography run.

In an arrangement (or with an automatic sampler), in which the metering device or the holding capacity thereof counts for the GDV, in this way, the GDV can be changed by a preset holding capacity (greater than 0 or deviating from a system-specific starting setting for the removal) before taking the sample, since this preset volume, which deviates from the standard position, counts for the GDV after switching over the paths (removal-injection).

Of course, however, it is also conceivable to set or vary the GDV during and/or after a sample injection. Preferably, a pump device (also already provided in a chromatography system), in particular a solvent pump, can be activated in opposition accordingly in this case, so that the resulting volume stream or the flow rate and/or the pressure in the path to the separating column, in particular before the entry thereof, is kept essentially constant (i.e., with a deviation from the existing flow rate or the existing pressure of less than 20%, for example, less than 10%, in particular less than 5%, preferably less than 1%) and damage to the separating column can be avoided and the reproducibility of the analysis can be ensured.

If the change of the GDV is performed, viewed in the flow direction to the column, after an introduced sample or a so-called sample plug (i.e., in the region between mixing point or occurrence of the gradient and injection point), the run time of the gradient also changes in relation to the position of the sample plug. Correspondingly, during the analysis, for example, during the increase of the GDV, chronological spreading or stretching of the result occurs (or of the components of the sample detected as peaks over time). However, if the change of the GDV or ΔGDV takes place, viewed in the flow direction of the column, before an introduced sample or a so-called sample plug (i.e., in the region between the injection point and entry of the separating column), the run time of the gradient remains unchanged in relation to the sample plug (no spreading), however, the result (or the detected peaks over time) occurs with a delay with the factor ΔGDV/flow rate.

If an already provided metering device is used as the volume adjustment device and the gradient flows through the metering device, a volume which is additionally set or varied in addition to a predefined sample volume counts for the GDV. In this embodiment of the invention, it is possible to set the desired GDV in a range from 0 or minimum of the metering device up to its maximum minus the predefined sample volume.

In a further embodiment of the invention, the smallest volume of the volume adjustment device can be set at the end of a chromatography run according to this, to shorten the time for washing out to a minimum.

In addition to the above-mentioned advantages (setting the GDV continuously and without manual intervention, cost-effective usage of an existing component for this purpose, possible saving of a mixer or assistance of the mixer), an undesired, excessively large GDV in the system can also be avoided or remedied according to the invention, by simply changing the GDV or the mixing volume. In any case, it is possible according to the invention, in contrast to conventional methods and systems, to meet all application-specific requirements for GDV and mixing performance, without replacing the corresponding components.

Although the GDV or mixing volume during a chromatography run is constant in conventional methods, it is furthermore also conceivable according to the invention to vary the GDV over the time of the analysis. If one block in HPG, for example, requires very little solvent in contrast to the other block, a higher GDV is then required to suppress the mixture irregularity. At another point in time, when both blocks require approximately equal amounts, a lesser GDV can be sufficient.

BRIEF DESCRIPTION OF THE DRAWINGS

The invention will be explained in greater detail hereafter on the basis of an exemplary embodiment illustrated in the drawing.

DETAILED DESCRIPTION OF EMBODIMENTS

Figure 1:
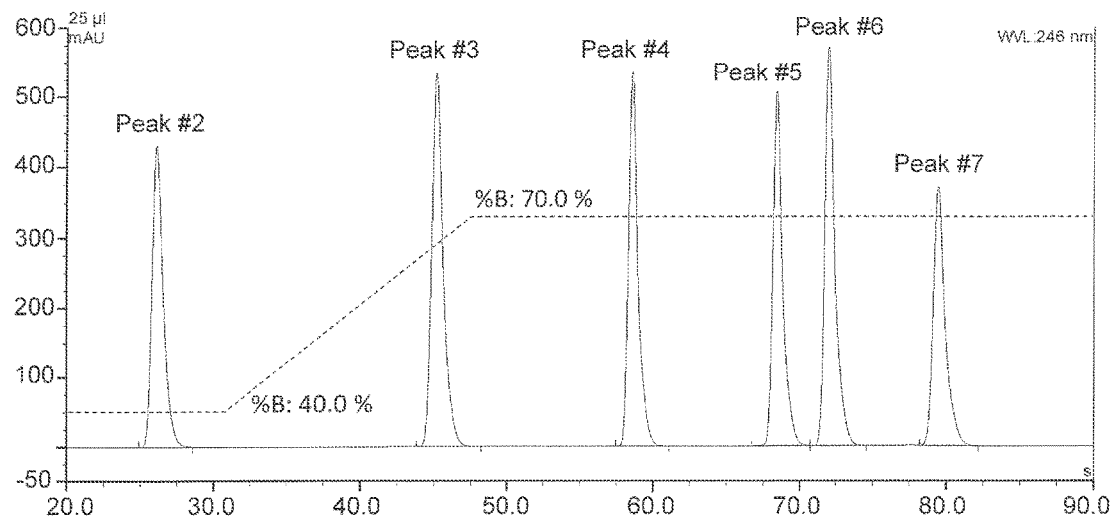
FIG. 1 shows two diagrams to illustrate the effect of two different GDVs during a chromatography run on the detected result.
Figure 1:
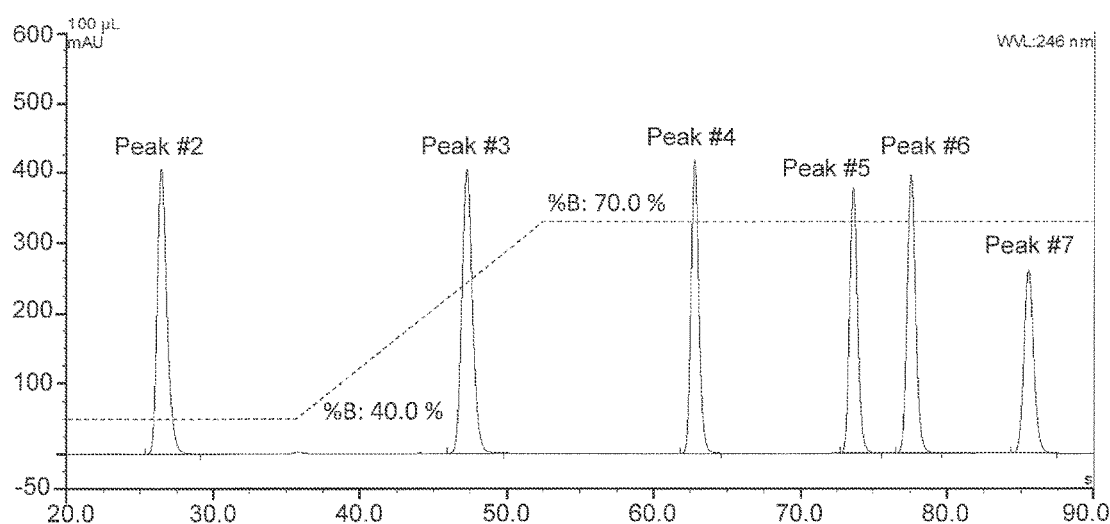

The diagrams illustrated in FIG. 1 show how a change of the GDV effects an analysis over time during a (sample) injection at the point in time 0 minutes. A solvent composition over time is shown as a dashed line in the diagrams. The solvent composition changes (transitions in the form of inflection points) from a constant (lower or front horizontal section) lower limit (acetonitrile 40%) via a varying (from 40% to 70% acetonitrile) composition or gradient (linear, rising, middle region) up to a constant (horizontal upper or rear section) upper limit (acetonitrile 70%). As the gradient, for example, a gradient having an increase of a solvent proportion B, for example, acetonitrile ACN, from 40%- 70% in 16 seconds (and corresponding reduction of the solvent proportion A or the remaining solvent proportions from 60%-30%) is used. In the upper diagram (case A), the preset pump volume of the volume adjustment device is $V_A=25$ µL, i.e., the GDV is increased by 25 µL, while in contrast in the lower diagram (case B), the adjusted pump volume is $V_A=100$ µL, i.e., the GDV is increased by 100 µL.

Since the increase of the GDV ($\Delta GDV=75$ µL=100 µL−25 µL) from case A to case B by the volume adjustment device, in particular a metering device 5 in the exemplary embodiment, viewed in the flow direction toward the (separating) column 41, with respect to the position of an introduced sample plug, is performed after the sample plug (i.e., following the rear separating surface between sample plug and solvent or between mixing point and tip of the sample needle 42), the incidence and therefore effect of the gradient or of a respective concentration with respect to the sample is shifted to the entry of the separating column 41, without the point in time of the incidence of the sample itself being delayed. As a result of the time shift or delay of the incidence of the respective concentration at the entry of the column 41, however, the eluting effect of the gradient on components to be eluted of the sample is shifted or delayed. As a result thereof, chronological spreading or stretching of the (sample) components detected as peaks occurs, which increases with components which are more difficult to elute (in the direction of the time axis).

As is apparent in FIG. 1 (lower diagram) as a detail of an analysis result (with illustrated peak 2 to peak 7 in mAU=milli absorption unit), the individual peaks occur with greater delay with increasing time in relation to their occurrence in the upper diagram, the later the corresponding components are eluted (due to a higher concentration). The points in time of the occurrence of the peaks increase accordingly as shown hereafter.

| | | |
|---|---|---|
| Peak 2 from 26.090 s to | 26.450 s | delay $\Delta t = 0.360$ s |
| Peak 3 from 45.150 s to | 47.250 s | delay $\Delta t = 2.100$ s |
| Peak 4 from 58.520 s to | 62.780 s | delay $\Delta t = 4.260$ s |
| Peak 5 from 68.390 s to | 73.630 s | delay $\Delta t = 5.240$ s |
| Peak 6 from 71.960 s to | 77.560 s | delay $\Delta t = 5.600$ s |
| Peak 7 from 79.430 s to | 85.520 s | delay $\Delta t = 6.090$ s |

The minimal delay at peak 2 is less than a measurement tolerance in this case, so that the occurrence thereof in case A to case B can be considered to be simultaneous or without delay. The reason for this is that the isocratic part of the solvent was already eluted at this peak 2, without a gradient already acting at this point in time.

In contrast, the amplitude or the maximum of the absorption can remain the same or be reduced, as is apparent from FIG. 1.

As a result of the GDV change $\Delta GDV$, the transitions or inflection points shift to the right between horizontal (isocratic) and the linear slope (gradient) on the time axis in the case of the transition horizontal to slope from 31 seconds to 36 seconds and in the case of the transition slope to horizontal from 47 seconds to 52 seconds in the comparison of the upper diagram to the lower diagram of FIG. 1. This delay of approximately 5 seconds results due to the higher GDV (lower diagram) by $\Delta GDV=75$ µL and the flow rate of 0.95 mL/min (=15.83 µL/s).

In contrast, if the increase of the GDV, viewed in the flow direction toward the column 41, takes place in position before the sample plug (i.e., between needle seat or injection port 45 and entry of the separating column 41 or before the front separating surface between sample plug and solvent), the detected result or peak of the components of the sample is delayed in time or shifted to the right in the diagram by the changed runtime without stretching.

FIG. 2 to FIG. 7 show, in a schematic illustration, an HPLC system having an automatic sampler 10 operating according to the split loop principle, which has a metering device 5, an injection valve 3, and a high-pressure pump 40. In addition, the automatic sampler 10 has a sample loop, which consists of a first connecting part 51, a second connecting part 52, 44, and a pump volume V (depending on the plunger position, minimum, $V_A$, $V_B$, or $V_C$ up to maximum $V_{max}$, of, for example, 120 µL). This can be a pressure-resistant line having a small diameter, for example, in the form of glass capillaries or stainless steel capillaries. The connecting part 51 is connected to a first sample loop port 16 of the injection valve 3 and to the sample delivery unit or the pump volume V thereof. The second connecting part, which consists of an aspirating part 44 and a supply part 52, is implemented as separable. For this purpose, the supply part 52 opens into an injection port 45, which is connected via the supply part 52 to a second sample loop port 13 of the injection valve 3. The aspirating part 44, which is connected at one end to the pump volume V of the metering device 5, has a sample needle 42 at the other end, using which the aspirating part 44 can be connected to the injection port 45.

However, the sample needle 42 can also be moved toward a sample container 43 and can aspirate a defined sample volume therefrom—in the manner described hereafter—into the aspirating part 44. Furthermore, the sample needle 42 can also be moved toward a container for a flushing fluid (not shown), to take flushing liquid therefrom for a flushing operation, using which the sample loops 51, 52, 44, the pump volume V, and optionally also the ports and grooves or channels of the injection valve can be cleaned. However, due to the special topology of the illustrated split loop principle, flushing of the sample loops 51, 52, 44 and of the sample delivery unit 5 is normally not necessary, since the latter are flushed through with solvent, which is delivered by the pump 40, in any case during an injection operation. However, the outer side of the sample needle 42 can be cleaned by the immersion in a container having cleaning or flushing liquid. Alternatively, the needle 42 can also be moved toward a washing and/or waste port (not shown in the drawing), to be cleaned and/or to discard excess solvent.

The metering device 5 comprises a syringe 50 in the illustrated embodiment, in which a plunger 53 is guided in a pressure-tight and displaceable manner. The plunger 53 is driven by means of a drive 55, for example, a stepping motor. The drive 55 is activated by a control unit 60. The control unit 60 also controls the switching operations of the injection valve 3 which has an activatable drive (not shown).

A waste port 12 of the injection valve is connected to a waste line 47, from which fluid can be discharged into a waste reservoir (not shown).

The high-pressure pump 40 is connected to a high-pressure port 15 of the injection valve. A chromatography column 41 is connectable to the further high-pressure port 14. The high-pressure pump 40 can be integrated as a component into the automatic sampler, however, it can also be provided in another unit or a separate pump unit.

The injection valve 3 consists of a stator 1 and a rotor 2. The stator 1 has the two high-pressure ports 14, 15, the two sample loop ports 13, 16, and the waste port 12. Of course, instead of the illustrated injection valve, injection valves having more than 5 ports are also conceivable for implementing the invention. Via these ports, the injection valve 3 is connected via the above-described connecting lines, which can be implemented as capillary connections, to the other functional elements of the HPLC system. The high-pressure screw connections required for this purpose are not shown for the sake of comprehensibility in FIG. 1. For reasons of simplicity, the injection valve is shown in the interface between stator 1 and rotor 2, wherein both the embodiment of the end face of the stator 1 and also the embodiment of the end face of the rotor 2 are shown to make it easier to understand the mode of operation. Inside the injection valve 3, the ports are implemented as boreholes, which lead to the other side of the stator 1. The rotor 2 has a number of curved grooves 21, 23, 25, which are aligned precisely with the boreholes of the input and output ports.

The rotor 2 is pressed with a contact pressure force against the stator 1, so that a mutual interface between rotor 2 and stator 1 is implemented, at which the two parts form a seal against one another. The contact pressure force is dimensioned in this case so that the arrangement is still leak-tight even at the highest pressures to be expected.

Figure 2:
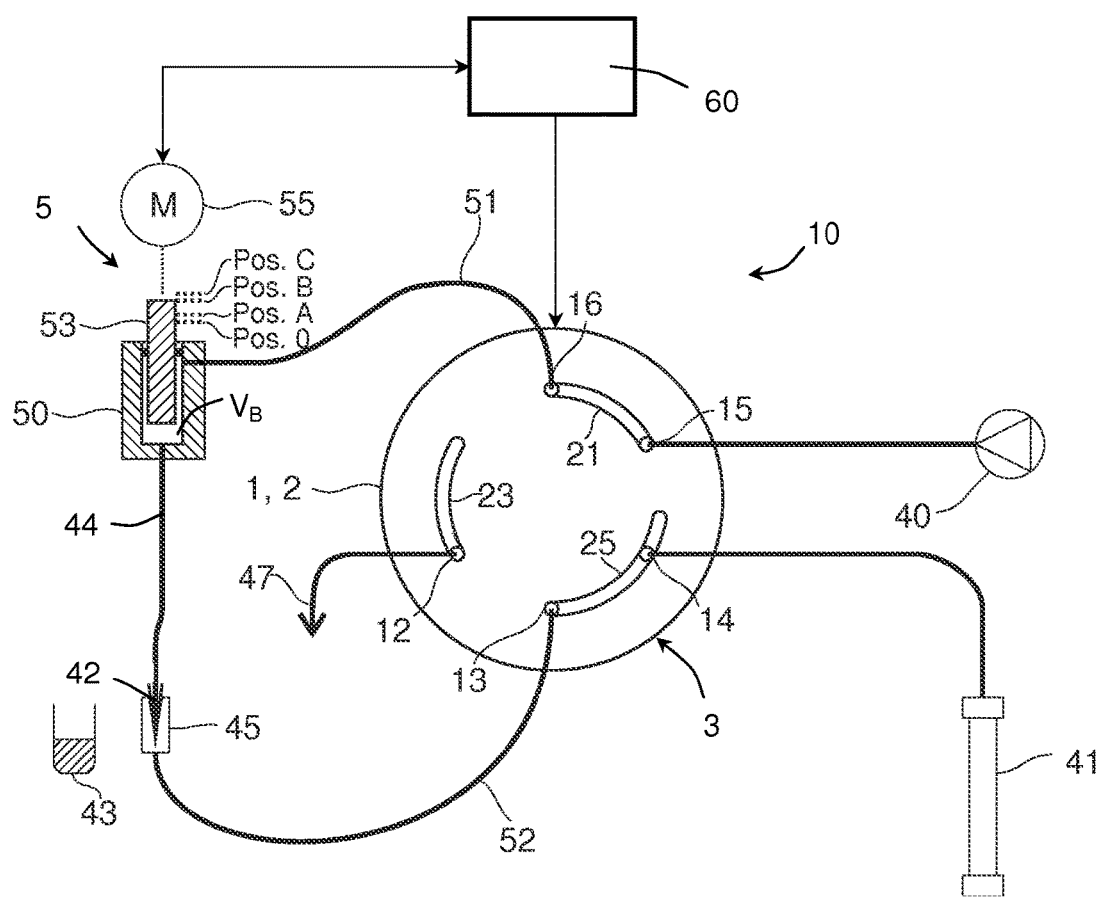
FIG. 2 shows a schematic illustration of an HPLC system having an automatic sampler according to the invention, to which a chromatography column is connected, wherein the injection valve is located in the INJECT position and an equilibration phase takes place in the illustrated state.

In the so-called equilibration phase of the system illustrated in FIG. 2, the switching or injection valve is located in the INJECT position, so that the pump actively flushes solvent through the sample loop in the direction of the column. A required GDV of the entire system or of the automatic sampler 10, which was determined during the method development or is already predefined, is adjusted by means of positioning of the plunger 53 during the equilibration (GDV of the entire system and additional ΔGDV of the metering device 5).

In the illustrated exemplary embodiment, a position Pos. B is assumed for this purpose, in which the metering device has a pump volume $V_B$. This volume already contains a desired change ΔGDV ($=V_A$) of the GDV of the automatic sampler 10 (or of its conventional GDV) and a desired sample quantity $V_{sample}$ ($=V_B-V_A$) to be received (at a later point in time), wherein, of course, other variants without including a sample volume at such a point in time are also conceivable.

A varied piston positioning during the equilibration and a therefore varied pump volume V of the volume adjustment device results in a changed pressure and flow (option 1), wherein the volume change can be compensated for in a preferred embodiment of the invention by adapting the flow rate, so that the pressure and flow still remain stable (option 2). The adaptation of the flow rate is performed in this case by activation of the pump 40 by the control unit 60, which opposes the metering device 5 accordingly.

Figure 3:
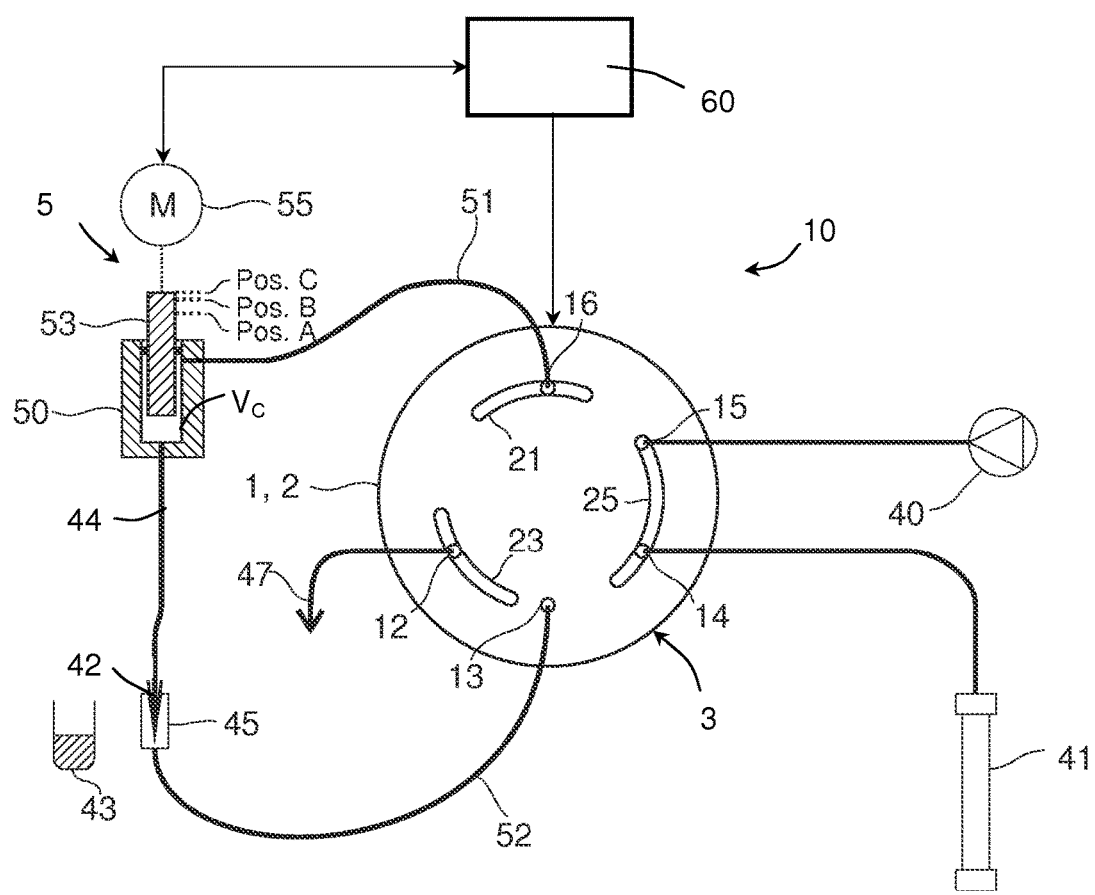
FIG. 3 shows the HPLC system in FIG. 2, wherein the injection valve was switched from the INJECT position into the PRESSURE EQUALIZATION position and the sample loop was switched out of the analytical path.

Subsequently, the valve 3, as shown in FIG. 3, switches into a PRESSURE EQUALIZATION position, in which the connecting part 51 and the second connecting part or the supply part 52 of the sample loop have no connection to the other components connected to the injection valve 3 and the sample loop is therefore switched out of the analytical path. The sample loop also has system pressure at this time (high pressure greater than 500 bar or even greater than 1500 bar).

In one variant (only required in the case of a method 1 explained hereafter), the drive 55 of the metering device 5 can move forward briefly, until the plunger 53 moves. In this case, the force on the plunger 53 or the torque of the drive 55 is measured and stored. It is a measure of the pressure in the sample loop (system pressure). In another variant, the pressure is ascertained or monitored by means of a sensor or the plunger position is detected and stored for later use.

Thereafter, the metering device 5 decompresses the sample loop by changing the plunger position from position B to position C or increasing the pump volume from $V_B$ to $V_C$ until almost to atmospheric pressure. In this case, the required movement path of the plunger 53 can be ascertained by measuring the force on the plunger 53 or the drive torque during the aspiration of the preceding sample or determined by a pressure sensor in the sample loop.

Figure 4:
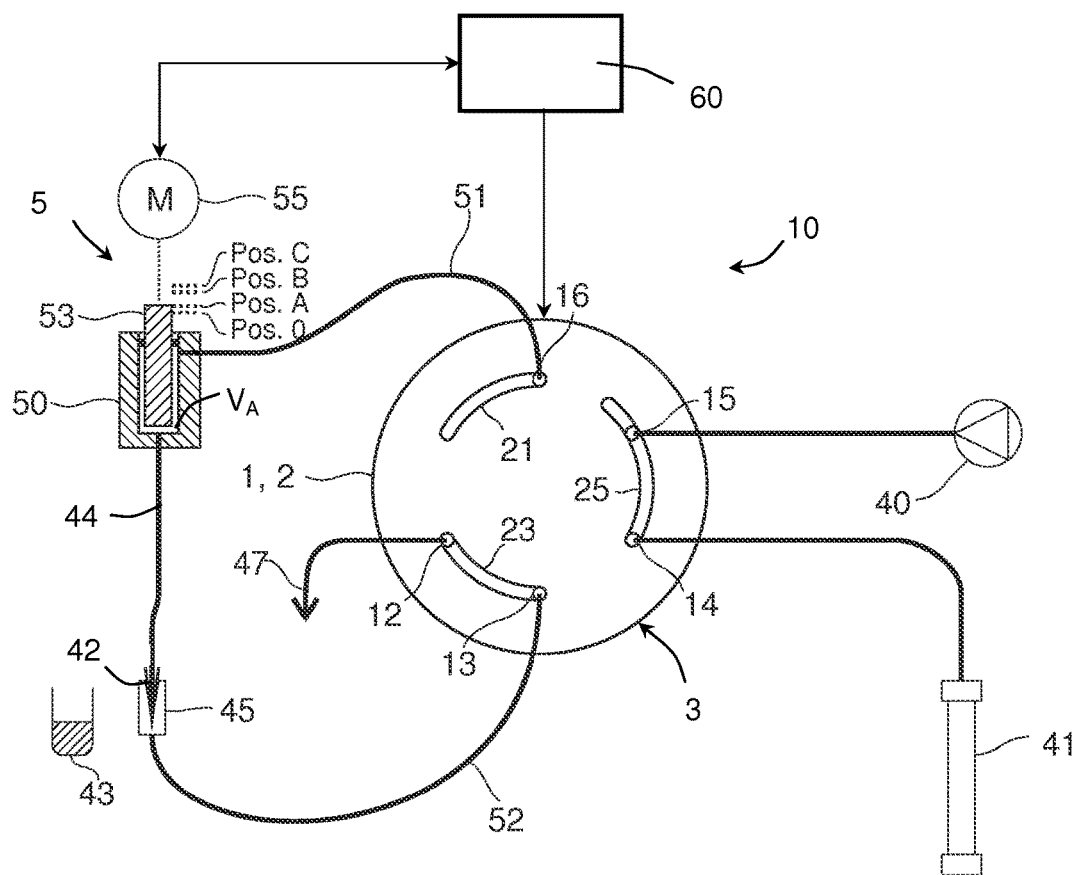
FIG. 4 shows the HPLC system in FIG. 3, wherein the injection valve was switched into the WASTE position.

As shown in FIG. 4, the switching valve 3 subsequently switches to the WASTE position, in which the quantity of solvent is expelled by the metering device 5, which corresponds to the sample quantity $V_{sample}$ ($=V_C-V_A$) to be aspirated.

Figure 5:
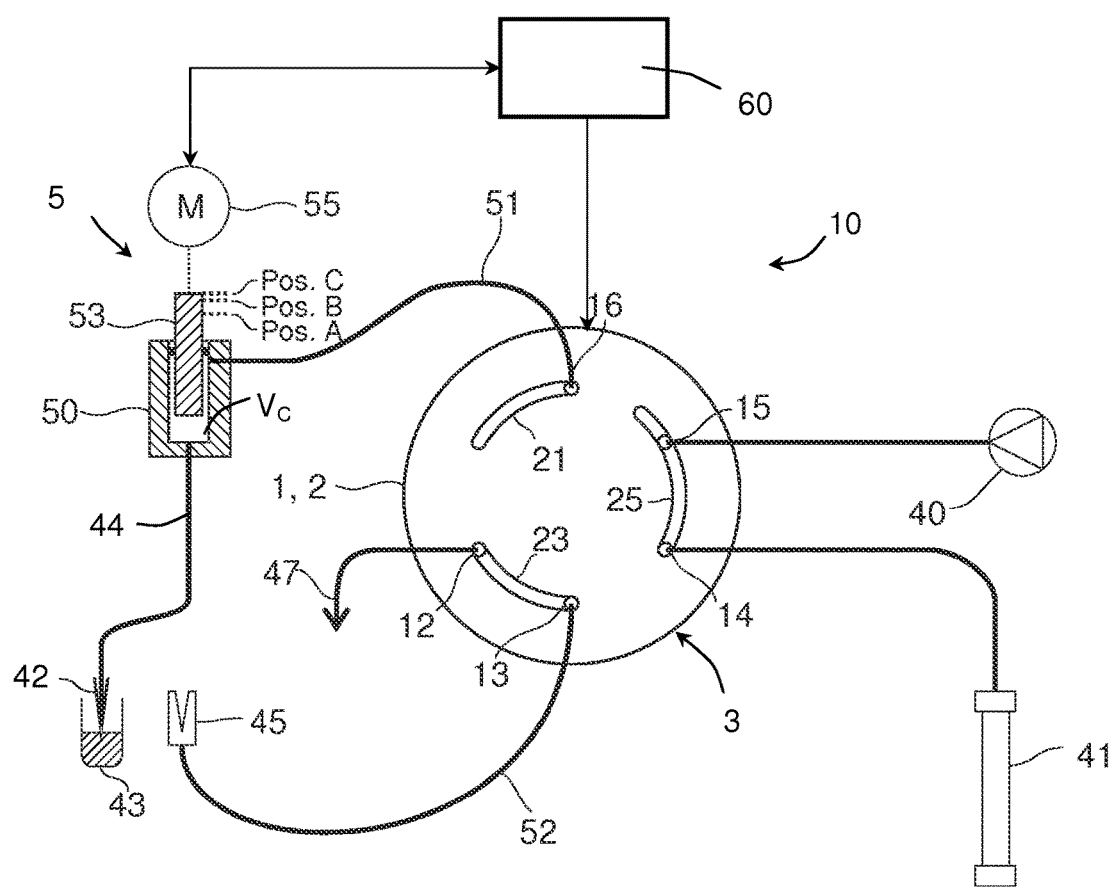
FIG. 5 shows the HPLC system in FIG. 4, wherein the sample needle was moved into the sample container to take a sample and subsequently the plunger of the syringe was moved into the end position (position C) to aspirate the sample volume.

In the state shown in FIG. 5, the sample needle 42 was subsequently moved into the sample container 43, so that a sample volume can be aspirated. For this purpose, the plunger 53 is initially in position A and is controlled by the control unit 60 for the aspiration in position C. In this case, the desired, defined sample volume $V_{sample}$ ($=V_C-V_A$) is aspirated into the aspirating part 44, wherein the volume of the sample is preferably less than the volume of the aspirating part 44, so that no mixing of the sample fluid with the fluid conveyed by the high-pressure pump can occur in the pump volume. FIG. 5 shows the state of the HPLC system after ending the aspiration operation.

In the first LOAD position of the valve 3 shown in FIG. 5, the grooves 21, 23, 25 are aligned with the ports 12 to 16 so that the grooves 23 and 25 connect the two high-pressure ports 14, 15 or the waste port 12 and the sample loop port 13. In this LOAD position, the high-pressure pump 40 therefore delivers fluid in the direction toward the chromatography column 41. Furthermore, the sample loop port 16 is closed pressure-tight.

During the aspirating, the force on the plunger 53 or the drive torque of the metering device 5 can be measured, wherein the drive torque or the plunger force represents a measure of the atmospheric pressure here and can be used as explained above during the decompression. Of course, it is also conceivable to ascertain, monitor, and/or store for later use the (atmospheric) pressure by means of a pressure sensor.

Subsequently, the switching valve 3 switches to a PRESSURE EQUALIZATION position, in which the connecting part 51 and the second connecting part or the supply part 52 of the sample loop do not have a connection to the other components connected to the injection valve 3. So as not to interrupt the flow through the chromatography column 41 during the delivery of the volume required for the compression of the sample loop content, the groove 25 in the rotor 2 of the valve is embodied as lengthened accordingly, so that the two high-pressure ports 14, 15 are also still connected in the PRESSURE EQUALIZATION position.

The sample loop is compressed in this case in one variant (method 1) until the stored (as explained above) drive torque or the plunger force is achieved as a measure of the system pressure. The pressure then again corresponds to the system pressure (high pressure). A compressibility of the sample which deviates from the solvent can cause the resulting plunger position to no longer correspond precisely under certain circumstances to the starting position, position B, of the plunger 53 in this case. In this way, exact precompression of the sample loop to the system pressure is performed with a small negligible deviation of the desired value $GDV_{target}$ of the GDV.

Figure 6:
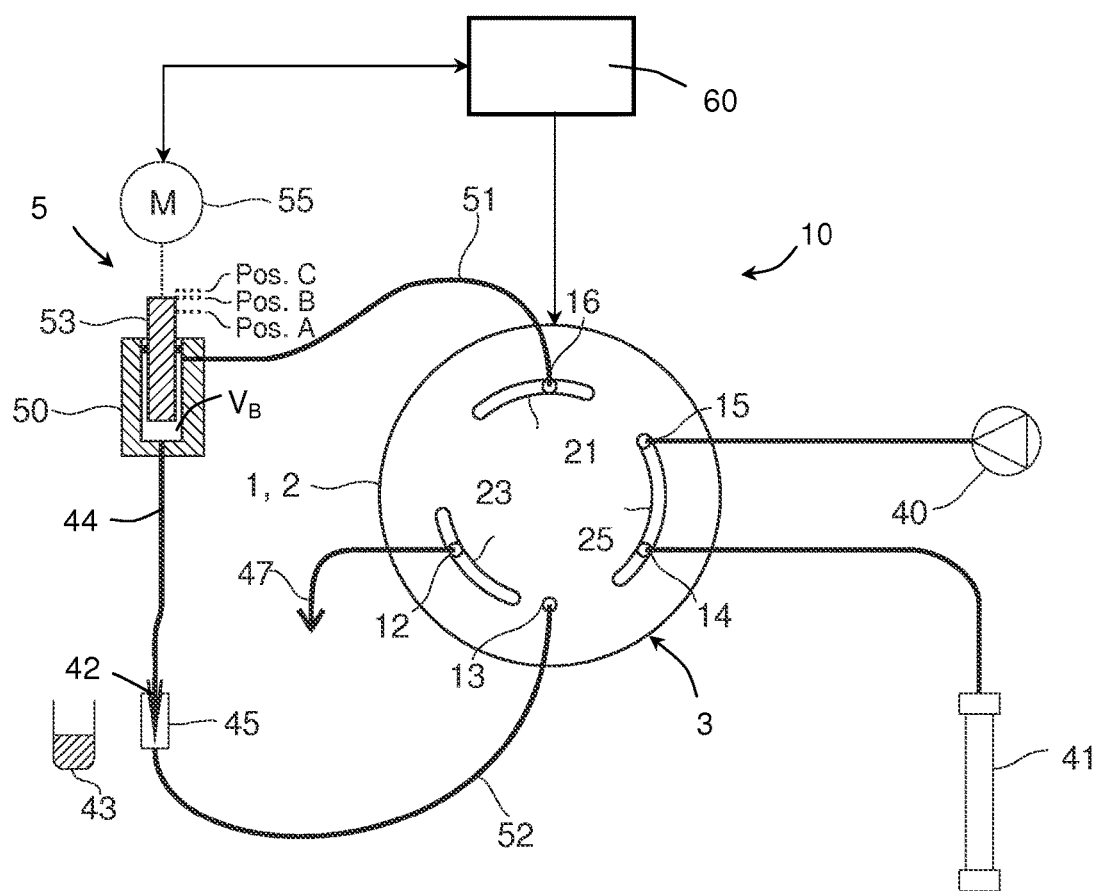
FIG. 6 shows the HPLC system according to FIG. 5, wherein the injection valve was switched from the LOAD position into the PRESSURE EQUALIZATION position and subsequently the plunger was moved into the position B for pressure equalization (pressure increase) in the sample loop.
Figure 7:
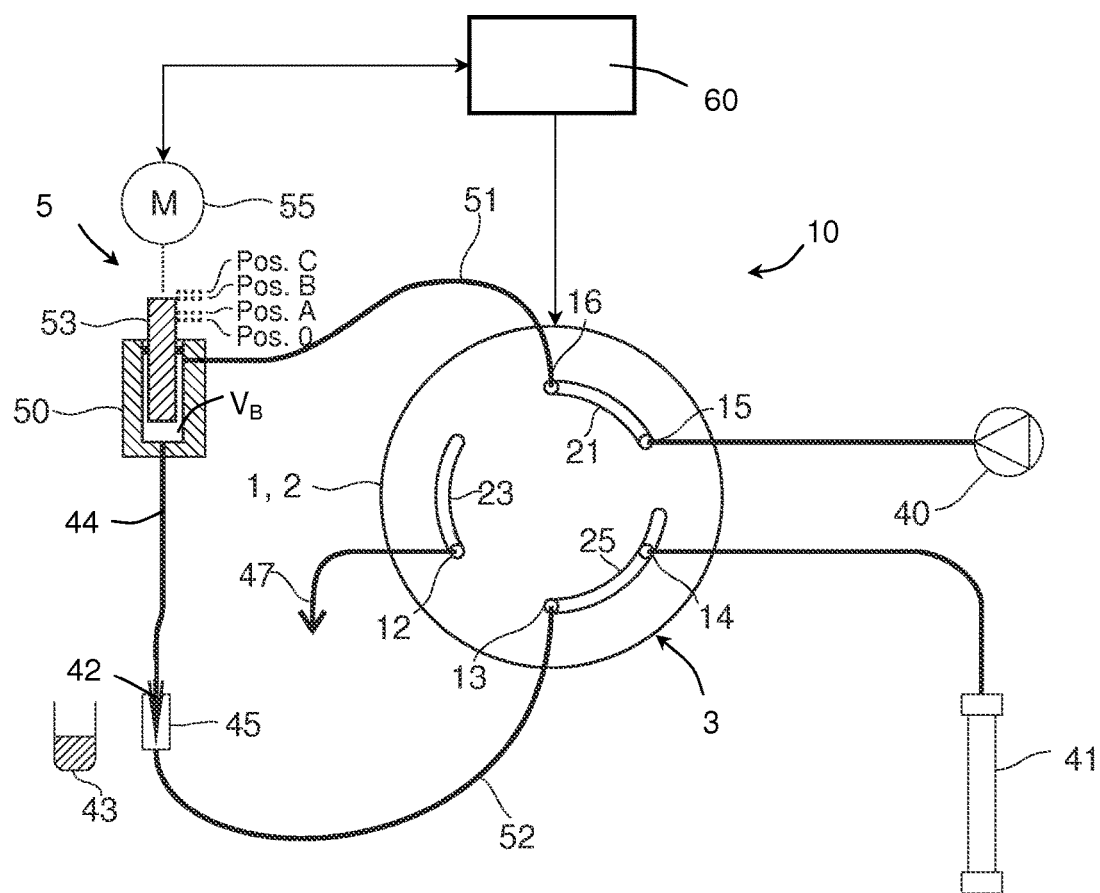
FIG. 7 shows the HPLC system in FIG. 6, wherein the injection valve was switched from the PRESSURE EQUALIZATION position into the INJECT position.

In another conceivable variant (method 2), the plunger 53, as shown in FIG. 6, is navigated to the starting position, position B, again and thus compresses the sample loop. In this case, deviations of the compressibility of the sample in comparison to the compressibility of the solvent result in slight deviations, which are to be neglected, from the system pressure. For this purpose, the achieved GDV corresponds exactly to the desired value $GDV_{target}$ of the GDV.

To be able to inject the sample volume which is located in the aspirating part 44, the sample needle 42 is moved into the injection port 45. This port seals off the needle tip so it is resistant to high pressure. Subsequently, the switching valve or injection valve 3 switches to the inject position, in which the aspirated sample volume is conveyed completely out of the aspirating part 44 to the column 41 (injection) by the solvent conveyed by the pump 40. If a gradient is navigated for the solvent (chronologically controlled mixing ratio of the solvent) for a chromatography run, no undesired delays advantageously result.

In a preferred embodiment of the invention, a deviation of the GDV caused by the precompression can be readjusted after the injection, wherein the correction movement of the plunger (to position B) is compensated for by corresponding adaptation of the flow rate. In this way, with exact precompression, an exact (adjusted or desired) $GDV_{target}$ can nonetheless be obtained. In addition, it is also possible (in particular if the sample volume after the compression is greater than the desired $GDV_{target}$) to readjust the desired $GDV_{target}$ during the chromatography run.

Although it is described differently in the exemplary embodiment, however, it is, of course, also conceivable to set or vary the GDV (deviating from a system-specific $GDV_{actual}$) to a desired amount $GDV_{target}$ also during a chromatography run instead of before. For this purpose, the pump 40 can be activated in opposition to the change of the metering device 5 accordingly via the control unit 60, to keep the flow rate or the volume stream to the column 41 constant.

Optionally, at the end of the chromatography run, the deviation $\Delta GDV$ ($=GDV_{target}-GDV_{actual}$) and therefore GDV or the mixing volume can be set to a minimum (minimal pump volume) by setting the plunger 53 at position 0, to shorten the washing-out time of the system, in particular of the sample loop.

LIST OF REFERENCE SIGNS 1 stator
2 rotor
3 injection valve
5 metering device
10 automatic sampler or chromatography system
12 waste port
13 second sample loop port
14 further high-pressure port
15 high-pressure port
16 first sample loop port
21, 23, 25 grooves
40 high-pressure pump
41 separating column
42 sample needle
43 sample container
44 aspirating part
45 injection port
47 waste line
50 syringe
51 first connecting part
52 supply part
53 plunger
55 drive
60 control unit
V pump volume
$V_A$ pump volume in position A
$V_B$ pump volume in position B
$V_C$ pump volume in end position C
$V_{sample}$ sample quantity
$V_{max}$ maximum volume of the metering device
Pos. 0 lowermost position of the plunger
Pos. A position A of the plunger
Pos. B position B of the plunger
Pos. C end position of the plunger
GDV gradient delay volume of the entire system
$GDV_{actual}$ system-specific value of the GDV
$GDV_{target}$ desired value of the GDV
$\Delta GDV$ deviation of the GDV due to corresponding plunger position

What is claimed is:

1. A method for setting a gradient delay volume of a liquid chromatography system for a chromatography run, the method comprising:
setting, and inputting into a control unit of the liquid chromatography system, a target gradient delay volume ($GDV_{target}$), wherein the target gradient delay volume is predefined based on an earlier chromatography run of another liquid chromatography system;
calculating, by the control unit, a difference of the gradient delay volume ($\Delta GDV$) between the target gradient delay volume and an actual gradient delay volume ($GDV_{actual}$) of the liquid chromatography system for the chromatography run;
controlling, by the control unit, a metering device of the liquid chromatography system, the metering device includes a syringe and a plunger, the plunger is configured to be guided in a pressure-tight and displaceable manner, and the metering device is configured to inject samples into an injection valve, wherein controlling the metering device is accomplished by moving the plunger within the syringe, the metering device having a variable pump volume V defined by the plunger, to adjust the pump volume V by adjusting a position of the plunger, in which the adjusted volume is equal to the calculated difference of the gradient delay volume; and performing the chromatography run on the liquid chromatography system using the adjusted volume and a solvent gradient, the liquid chromatography system further comprising the injection valve, a pump connected to a first port of the injection valve, a separation column connected to a second port of the injection valve, and a sample loop extending between a pair of sample loop ports of the injection valve, wherein the metering device is in the sample loop.

2. The method of claim 1, in which the difference of the gradient delay volume is calculated with an equation, the equation comprising:

$$\Delta GDV = GDV_{target} - GDV_{actual}, \text{ where}$$

$\Delta GDV$ is the difference of the gradient delay volume due to the position of the plunger within the metering device, $GDV_{target}$ is the target gradient delay volume, and $GDV_{actual}$ is the gradient delay volume of the liquid chromatography system.

3. The method of claim 1, in which the liquid chromatography system includes an injection port selectively connected to the separation column via fluidly interconnected components, in which the actual gradient delay volume is a holding capacity of fluidly interconnected components extending from the adjustment device to the separation column.

4. The method of claim 1, in which the calculating the difference of the gradient delay volume calculates a difference that is less than or equal to 1000 microliters.

5. The method of claim 1, in which the performing of the chromatography run step includes a sample injection, in which the setting of the target gradient delay volume occurs after the sample injection.

6. The method of claim 5, in which the controlling the volume adjustment device step includes adjusting the plunger of the pump to compensate for the adjusted volume V of the metering device so that the flow rate and pressure entering the separation column is essentially constant.

7. The method of claim 1, in which the performing of the chromatography run step includes a sample injection, in which the setting of the target gradient delay volume occurs before the sample injection.

8. The method of claim 1, wherein the performing of the chromatography run step includes, at the end of the chromatography run, adjusting the position of the plunger in the metering device so that the volume of the metering device is zero.

* * * * *